(12) United States Patent
Ferko

(10) Patent No.: US 8,226,725 B2
(45) Date of Patent: Jul. 24, 2012

(54) PROSTHESIS HAVING A SOFT TISSUE ATTACHMENT ELEMENT

(75) Inventor: Michael Ferko, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 68 days.

(21) Appl. No.: 12/551,692

(22) Filed: Sep. 1, 2009

(65) Prior Publication Data
US 2011/0054625 A1    Mar. 3, 2011

(51) Int. Cl.
*A61F 2/38* (2006.01)
(52) U.S. Cl. .................. 623/20.14; 623/13.12
(58) Field of Classification Search ............... 623/13.11, 623/13.12, 13.14, 13.18, 20.14
See application file for complete search history.

(56) References Cited

U.S. PATENT DOCUMENTS

| | | | |
|---|---|---|---|
| 3,803,641 A | 4/1974 | Golyakhovsky et al. |
| 3,979,778 A | 9/1976 | Stroot |
| 3,988,783 A | 11/1976 | Treace |
| 4,045,826 A | 9/1977 | Stroot |
| 4,246,660 A | 1/1981 | Wevers et al. |
| 4,355,427 A | 10/1982 | Schneider |
| 4,714,475 A | 12/1987 | Grundei et al. |
| 4,790,850 A | 12/1988 | Dunn et al. |
| 4,790,854 A | 12/1988 | Harder et al. |
| 5,171,322 A | 12/1992 | Kenny |
| 5,330,531 A | 7/1994 | Capanna et al. |
| 6,200,350 B1 | 3/2001 | Masini |
| 6,267,785 B1 | 7/2001 | Masini |
| 6,267,788 B1 | 7/2001 | Andersson |
| 6,334,874 B1 | 1/2002 | Tornier et al. |
| 6,371,985 B1 | 4/2002 | Goldberg |
| 6,379,391 B1 | 4/2002 | Masini |
| 6,383,225 B2 | 5/2002 | Masini |
| 6,398,812 B1 | 6/2002 | Masini |
| 6,558,425 B2 | 5/2003 | Rockwood, Jr. |
| 6,592,622 B1 | 7/2003 | Ferguson |
| 6,821,300 B2 | 11/2004 | Masini |
| 7,001,429 B2 | 2/2006 | Ferguson |
| 7,070,622 B1 | 7/2006 | Brown et al. |
| 7,175,664 B1 | 2/2007 | Lakin |
| 7,229,478 B2 | 6/2007 | Masini |
| 2003/0216809 A1 | 11/2003 | Ferguson |
| 2007/0078516 A1 | 4/2007 | Emami |
| 2008/0021554 A1 * | 1/2008 | Stone et al. ................. 623/13.18 |
| 2011/0130840 A1 | 6/2011 | Oskouei |

FOREIGN PATENT DOCUMENTS

| | | |
|---|---|---|
| GB | 2126095 A | 3/1984 |
| GB | 2253566 A | 9/1992 |

OTHER PUBLICATIONS

Stryker, "MRS Upper Extremity: Surgical Protocol", 40 pages, (1988).

(Continued)

*Primary Examiner* — Thomas J Sweet
*Assistant Examiner* — Matthew Schall
(74) *Attorney, Agent, or Firm* — Lerner, David, Littenberg, Krumholz & Mentlik, LLP

(57) ABSTRACT

A prosthetic bone implant, the bone implant forming one side of a joint and including a prosthesis and a soft tissue attachment component. The soft tissue attachment component is connected to the bone implant and extends outwardly therefrom and towards a joint line. The soft tissue attachment component is moveable with respect to the prosthesis while connected thereto.

13 Claims, 22 Drawing Sheets

OTHER PUBLICATIONS

Maiawer et al., "Proximal Humerus Resection, The Tikhoff-Linberg Procedure and its Modifications", 33 pages (1984).

International Search Report, PCT/US2010/047499, Dated Feb. 18, 2011.

* cited by examiner

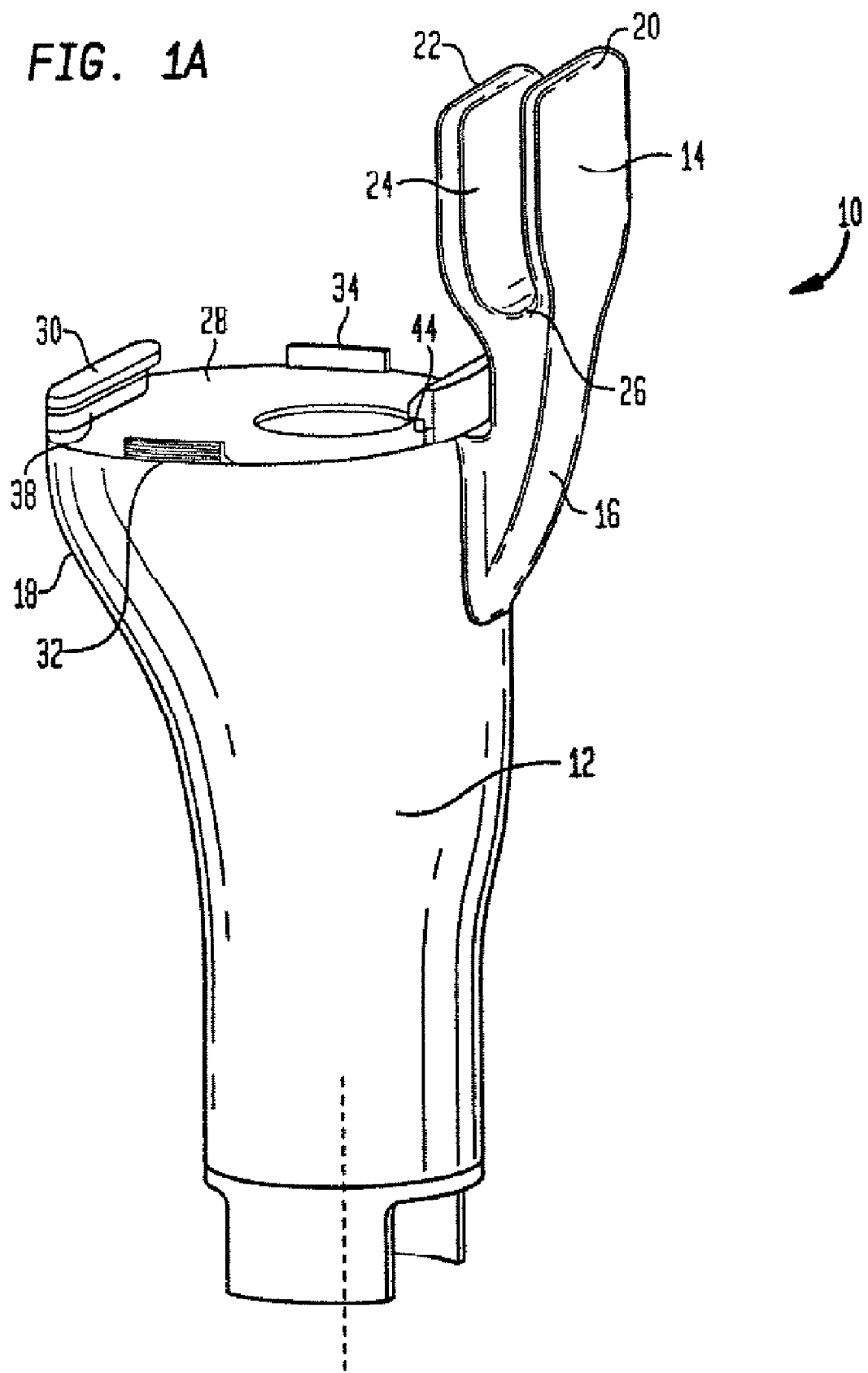

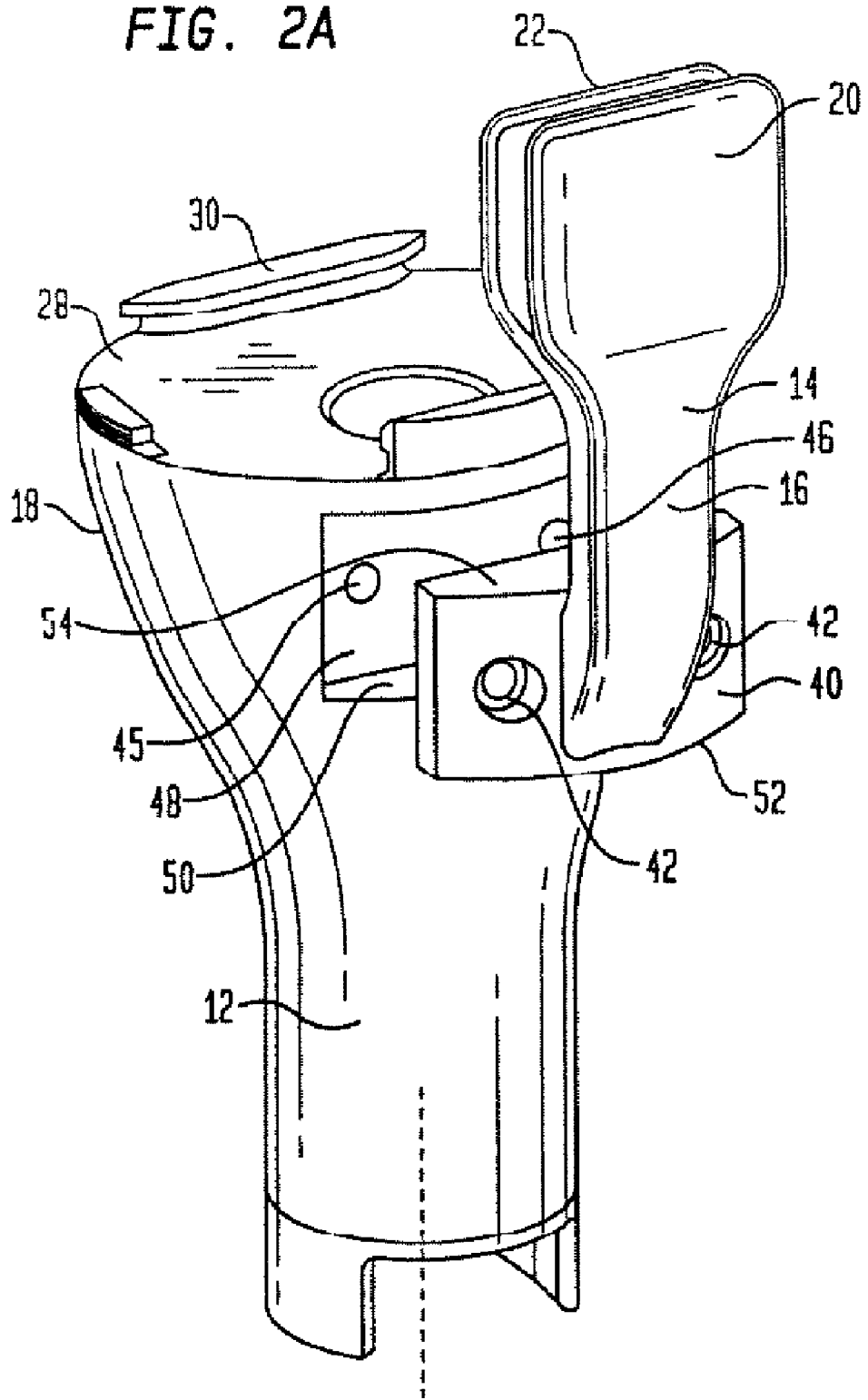

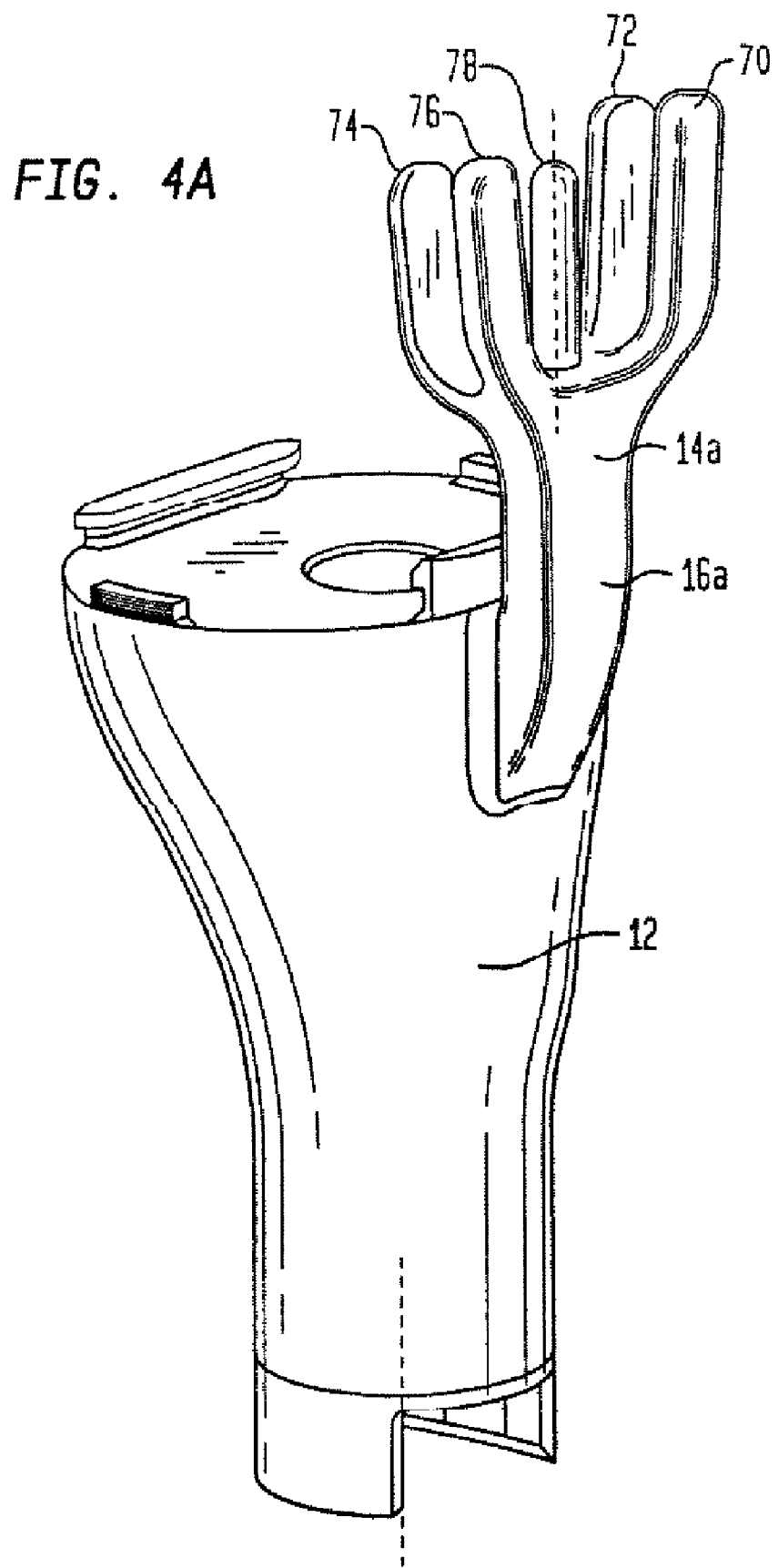

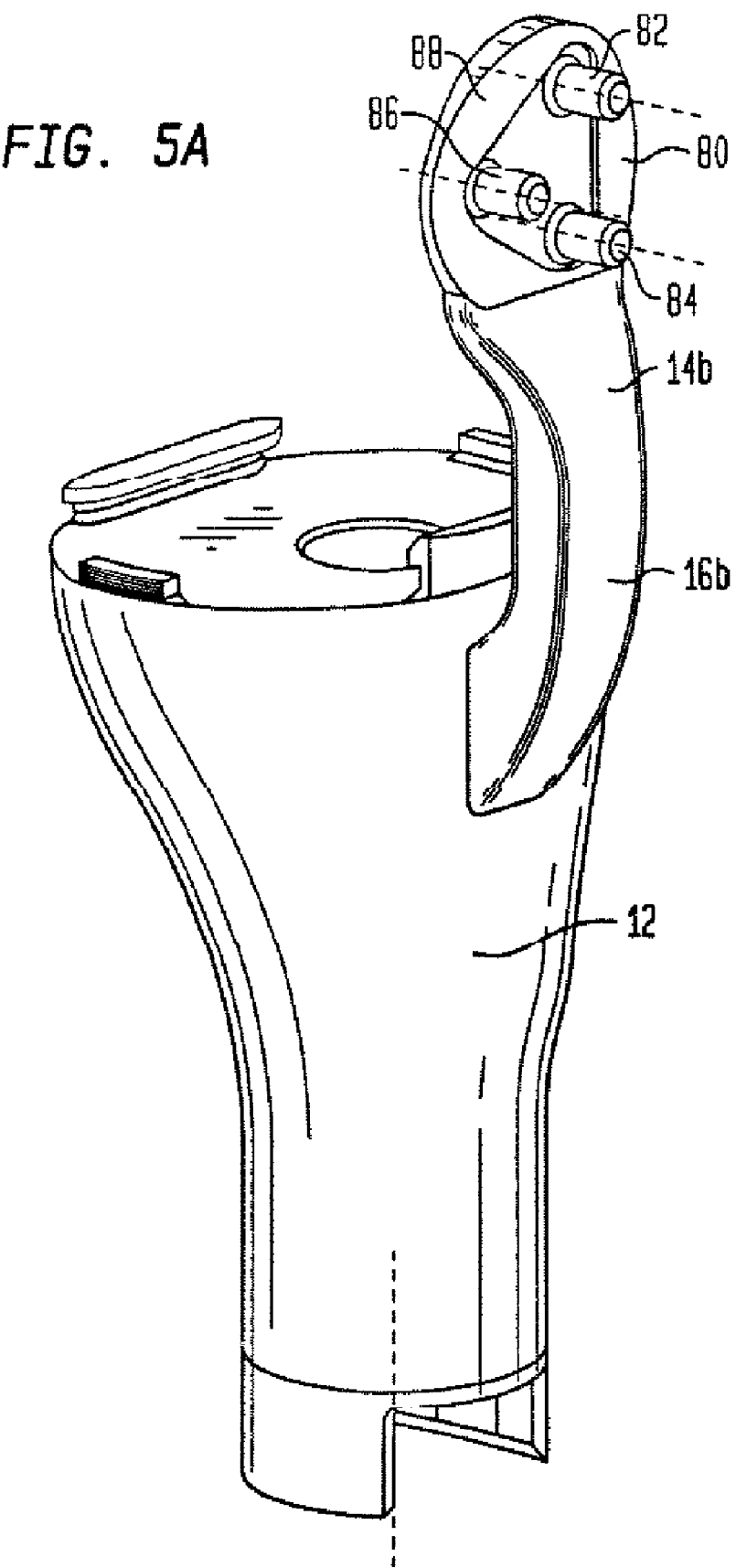

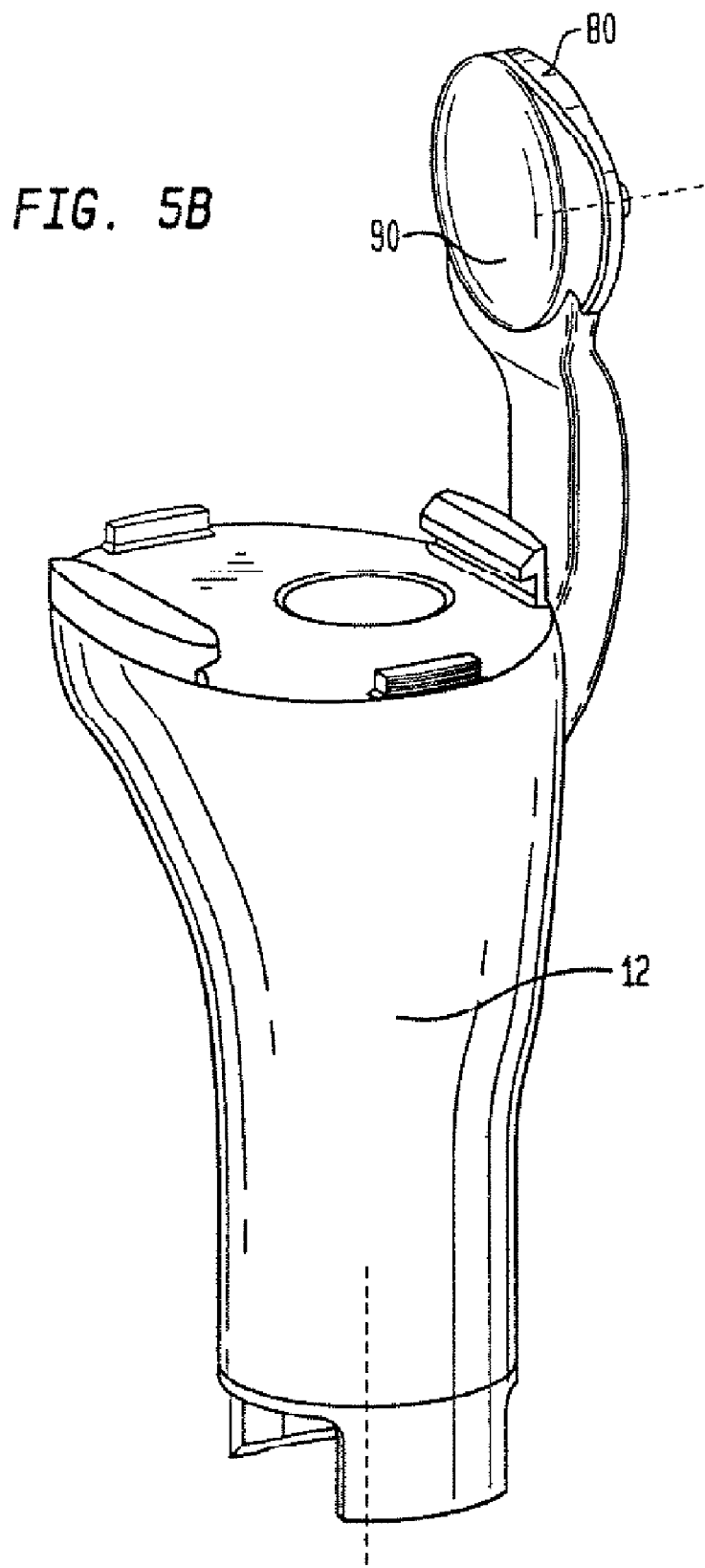

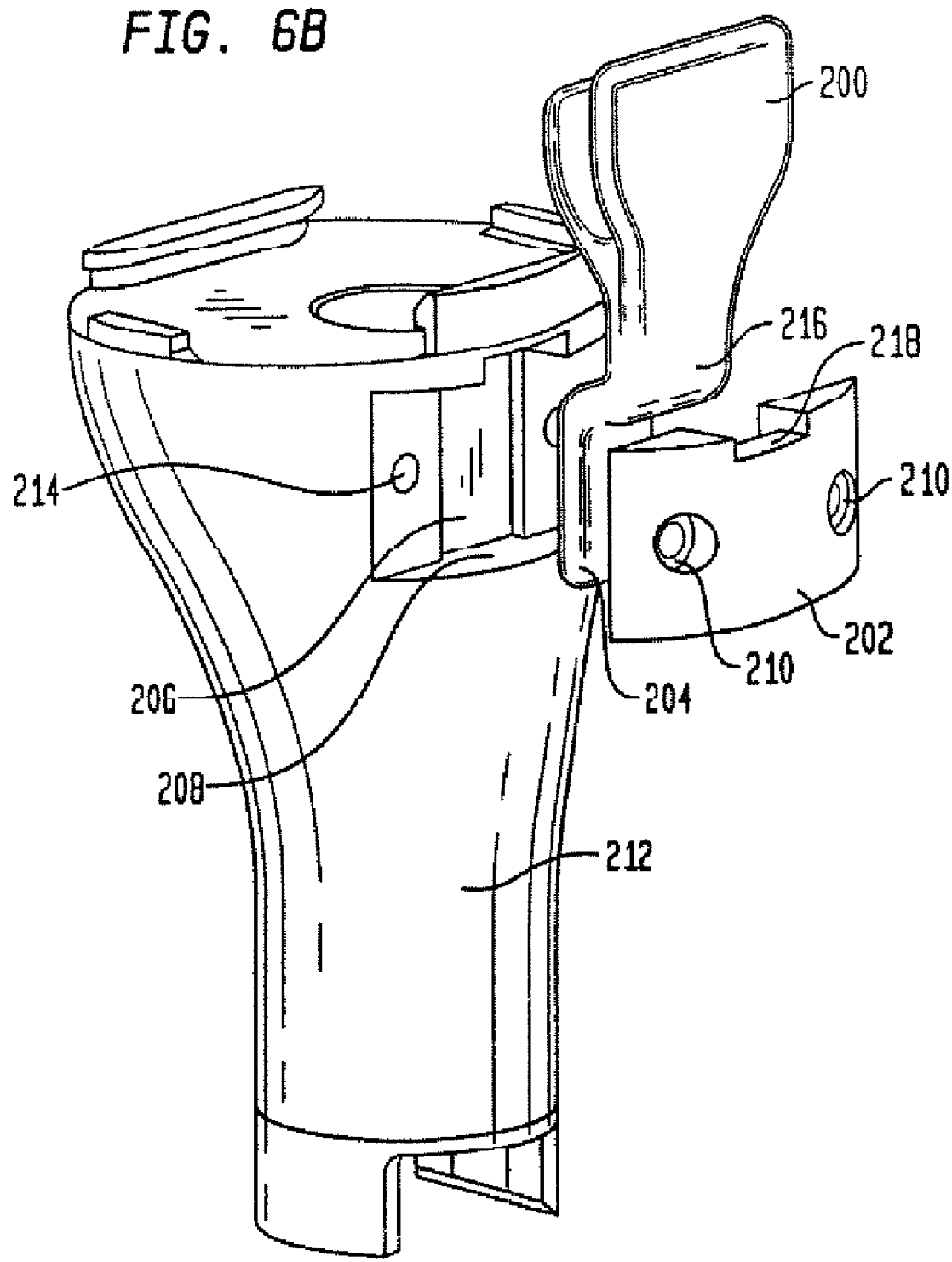

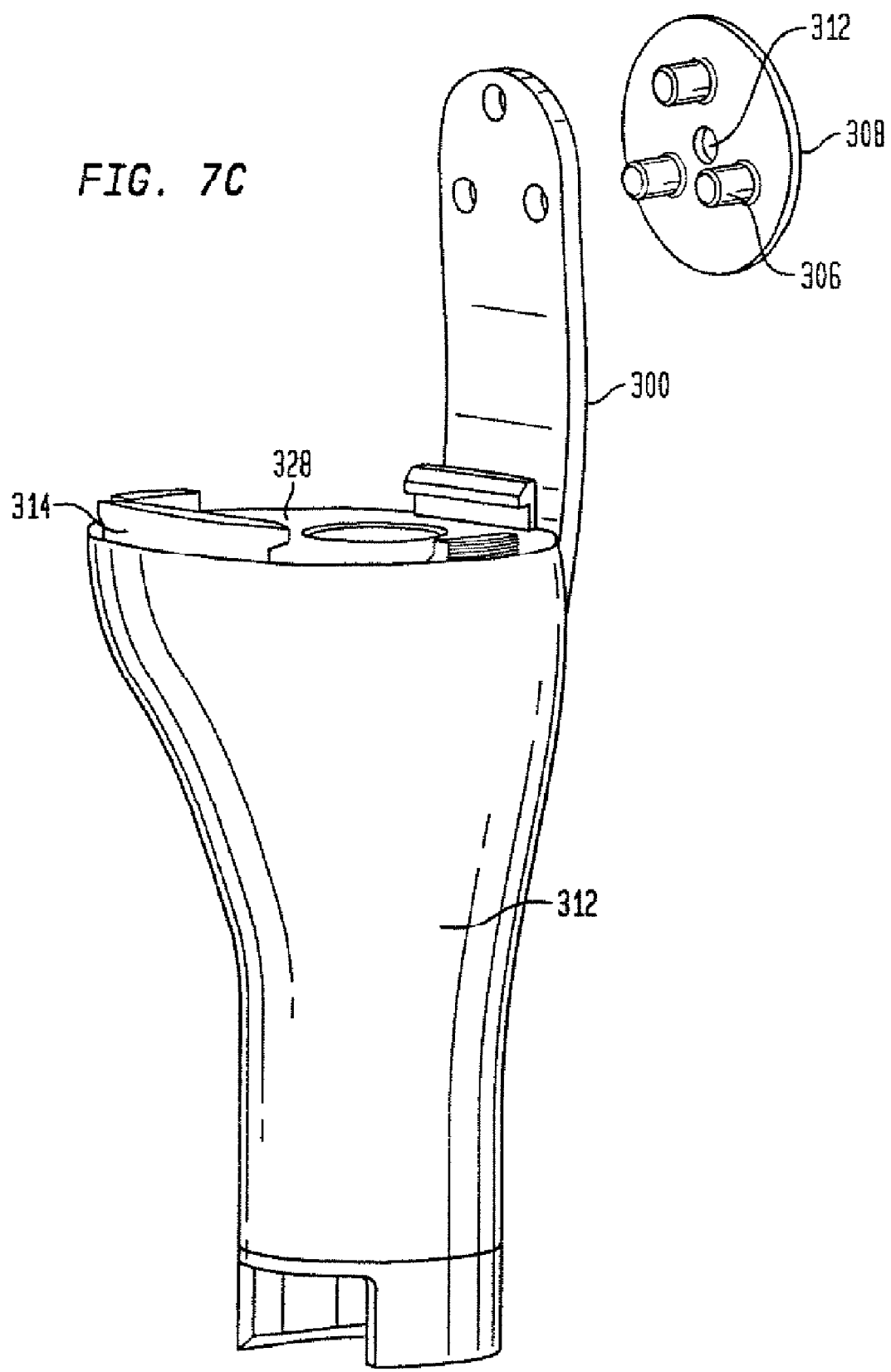

PROSTHESIS HAVING A SOFT TISSUE ATTACHMENT ELEMENT

FIELD OF THE INVENTION

The present technology relates to surgical procedural devices. The present technology can be used, for example, to attach soft tissue such as tendinous tissue to a bone prosthesis.

BACKGROUND OF THE INVENTION

Certain surgical procedures require the resection of bone where critical soft tissues, such as tendons, ligaments and muscles, in particular the patella tendon, attach to the bone. It has been difficult to secure attachment of these soft tissues to prosthesis for multiple reasons.

First, in natural attachment to bone, there is transition region of soft tissue to bone (i.e., muscle-tendon-bone) that has a gradual change from flexible to rigid. In the reattachment of soft tissue to bone, this transition region is often lost resulting in failure of the soft tissue prosthesis interface from the flexibility of soft tissue to the very rigid metal implant.

Second, in certain procedures resection of surrounding soft tissues along with bony resections are required (i.e., resection to obtain adequate surgical margins during the removal of bone cancer such as osteosarcoma). This soft tissue resection often leaves the remaining soft tissues too short to reach their original attachment sites, even if adequate method of attachment directly to metal were available.

Currently, several methods are used to create a functional bridge between soft tissue and prosthesis, which exhibit limited success. Where there exists enough length for the soft tissue to reach the prosthesis, the soft tissue is often sutured directly to the prosthesis. Advances have been made in the material and surface treatment of the attachment sites (i.e., the use of porous or foam metals) to improve and promote the in-growth of soft tissue after surgery. However, the relative stiffness of these attachment sites compared to the soft tissue being attached continues to be a problem.

When soft tissue length is not adequate to reach the natural attachment site on the prosthesis, a graft is sometimes used to create a bridge. Autograft (via transplant or flap) can help to provide additional functional length of the soft tissue, but does not address the stiffness issue. Also, function of the graft host site is reduced. Allograft is also an option, however, again stiffness is not addressed and known issues of rejection and/or lack of integration with the graft tissue exist. Synthetic materials such as aorta-graft materials have been used to create a sleeve or bridge between the prosthesis and bone. This can address the stiffness issue at the soft tissue attachment site. However, the lack of direct integration of the synthetic material with the prosthesis means that long term loads must be borne by sutures or other suitable materials are used to secure the graft to the prosthesis. As a result, failure of the interface merely moves from the soft tissue/prosthesis interface to the graft/prosthesis interface.

In all of the above cases, the preparation and attachment of all of these grafts requires significant time and effort during the surgical setting, which exposes the patient to additional OR time in what can be an already lengthy surgical procedure.

BRIEF SUMMARY OF THE INVENTION

One aspect of the present technology provides a prosthetic bone implant, the bone implant forming one side of a joint and comprising a prosthesis and a soft tissue attachment component connected to the bone implant and extending outwardly therefrom and towards a joint line. The soft tissue attachment component may be moveable with respect to the prosthesis while connected thereto. Furthermore, the soft tissue attachment may extend beyond the joint line and have a first end and a second end, the first end configured to attach to the prosthesis and the second end including a tip, such as, for example, a forked tip configured to engage a soft tissue.

In one embodiment, the prosthetic bone implant may further comprise a plurality of filaments attached to the soft tissue attachment component, wherein the filaments are configured to connect the soft tissue attachment component to soft tissue. Alternatively, the soft tissue attachment component may have a first end and a second end, the first end configured to attach to the prosthesis and the second end including a plug configured for attachment to bone. In yet another embodiment, the soft tissue attachment component may have a first end and a second end, the first end configured to attach to the prosthesis and the second end attached to a replacement or resurfacing element for a bony structure. The soft tissue attachment component may be formed integrally with the replacement or resurfacing element. Furthermore, the soft tissue attachment component may have a sufficient length to provide attachment to a piece of soft tissue that has been at least partially resected.

The soft tissue attachment may extend from a region of the prosthetic configured to promote ingrowth or on-growth of the soft tissue, such as a porous or foam metal, and hence load share with the soft tissue. The soft tissue attachment mechanism may extend toward or beyond the soft tissues natural attachment site from a region distal to (away from the joint line) the natural attachment site so that when tissue prosthesis integration occurs, it will be at the natural site.

In another embodiment, the prosthesis and the soft tissue attachment component may be formed as a one-piece construct. Alternatively, the prosthesis and the soft tissue attachment mechanism may be configured to be connected at the time of surgery. In addition, the soft tissue attachment component may be configured to be modified by a surgeon according to the size and tension needs of a particular procedure.

The soft tissue attachment component of the prosthetic bone implant may be composed of a material that is either synthetic or biologic, or a composite of synthetic and biologic materials. Furthermore, the soft tissue attachment component may be composed of a material that is biodegradable or bioresorbable such that over time it is replaced by natural tissue. Still furthermore, the soft tissue attachment component may be at least partially porous. In one embodiment, the soft tissue attachment component may have a variable porosity throughout its length or throughout its cross section, or throughout both its length and its cross section.

The soft tissue attachment component of the prosthetic bone implant may be composed at least in part of a material selected from the group consisting of silk mesh or resorbable mesh, Dacron, polytetra fluoroethylene, Texturized or Openweave poly(ethylene terephthalate), waterswolen poly(2-hydroxyethyl methacrylate), polydioxanone, PDO/Elastin Weave, polyurethane, aromatic porous polyurethane, poly-(L-lactic acid), Polyetheretherketone, allograft or xenograft tendon or ligament, small-intestinal submucosa, collagen, cell seeded collagen matrices, hydrogels, Chitosan, or other known cell scaffold materials.

A further aspect of the invention provides a method of securing soft tissue to a prosthetic bone implant. The method may comprise implanting a joint bone prosthesis adjacent to a joint at or near a natural soft tissue attachment site, the prosthesis connected to a one-piece soft tissue attachment component. The method may also include suturing the soft tissue attachment component to the natural soft tissue with filaments.

In one embodiment of the method, the step of attaching the soft tissue attachment component to natural soft tissue may include fixing the natural soft tissue between the prongs of a forked end of the soft tissue attachment component. In another embodiment, attaching the soft tissue attachment component to natural soft tissue may include suturing the natural soft tissue to the soft tissue attachment component with filaments connected to the end of the soft tissue attachment component. Other embodiments may include attaching the soft tissue attachment component to a bony structure by implanting a plug into the bony structure, wherein the plug is connected to the soft tissue attachment component, or attaching the soft tissue attachment component to a bony structure by fixing a replacement or resurfacing component to the bony structure, where the replacement or resurfacing component is connected to the soft tissue attachment component.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

The present technology will be better understood on reading the following detailed description of nonlimiting embodiments thereof, and on examining the accompanying drawings, in which:

FIG. 1a is an isometric view of a prosthetic tibial implant including the soft tissue attachment device of the present invention;

FIG. 2a is a prosthetic tibia including a modular soft tissue attachment device of the present invention;

FIG. 3b is an anterior view of the prosthetic component of FIG. 3a;

FIG. 4a is an isometric view of a prosthetic tibial implant having yet an additional alternate embodiment of the soft tissue attachment device of the present invention;

FIG. 4b is an anterior view of the prosthetic tibial component of FIG. 4a;

FIG. 5a is an isometric view of yet another alternate soft tissue attachment device of the present invention showing a tibial prosthesis with a proximally extending soft tissue attachment component with resurfacing element;

FIG. 5b is a posterior view of the prosthetic tibial component of FIG. 5a;

FIG. 6B is an isometric view of the embodiment of FIG. 6A with the soft tissue attachment element disassembled from the prosthetic tibia;

FIG. 7c is a posterior view of the embodiment of FIGS. 7a and 7b with the prosthetic patella disassembled from the soft tissue attachment device.

DETAILED DESCRIPTION

Figure 1B:
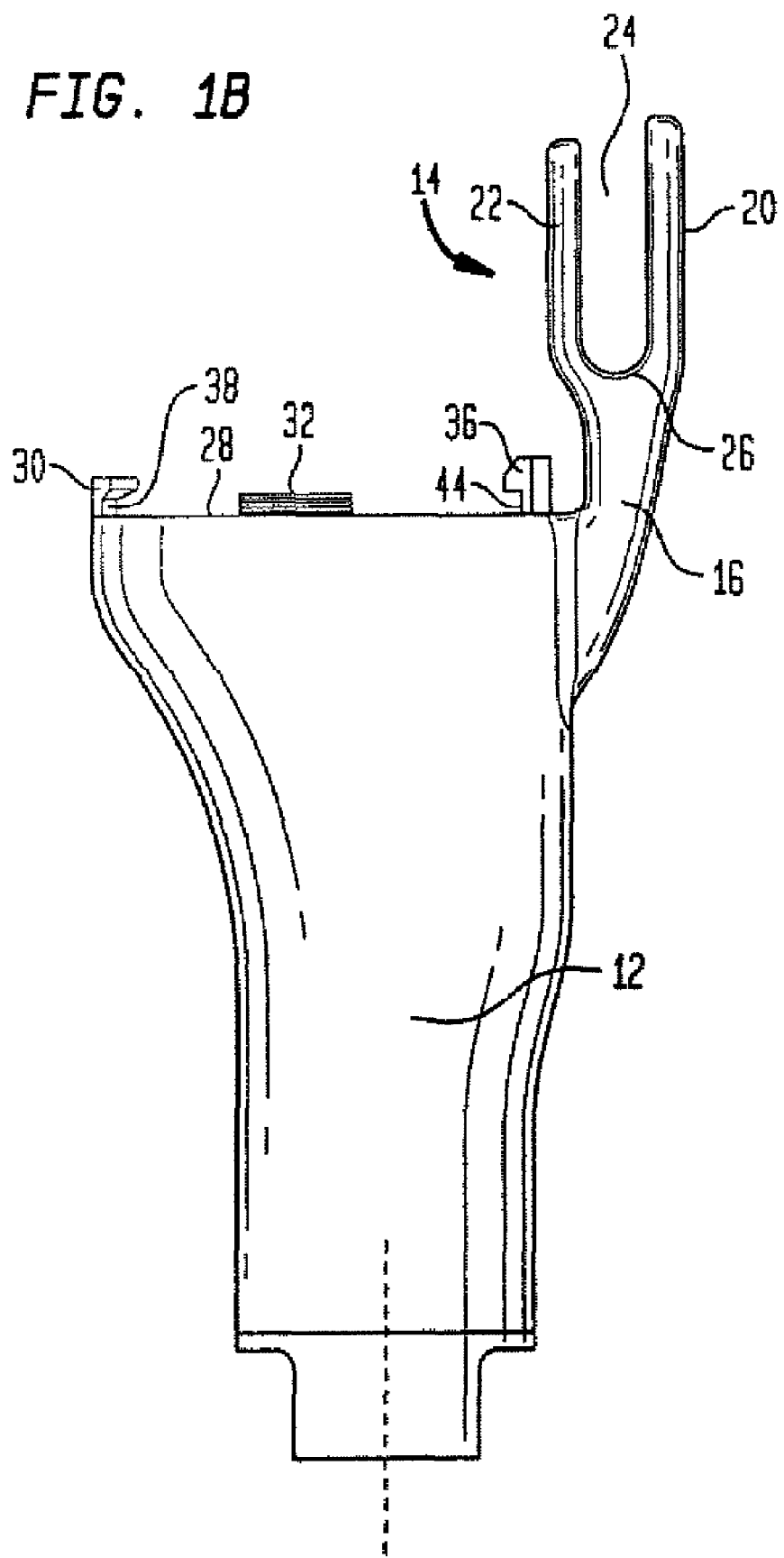
FIG. 1b is a lateral view of the tibial implant including soft tissue attachment device of the present invention.
Figure 1C:
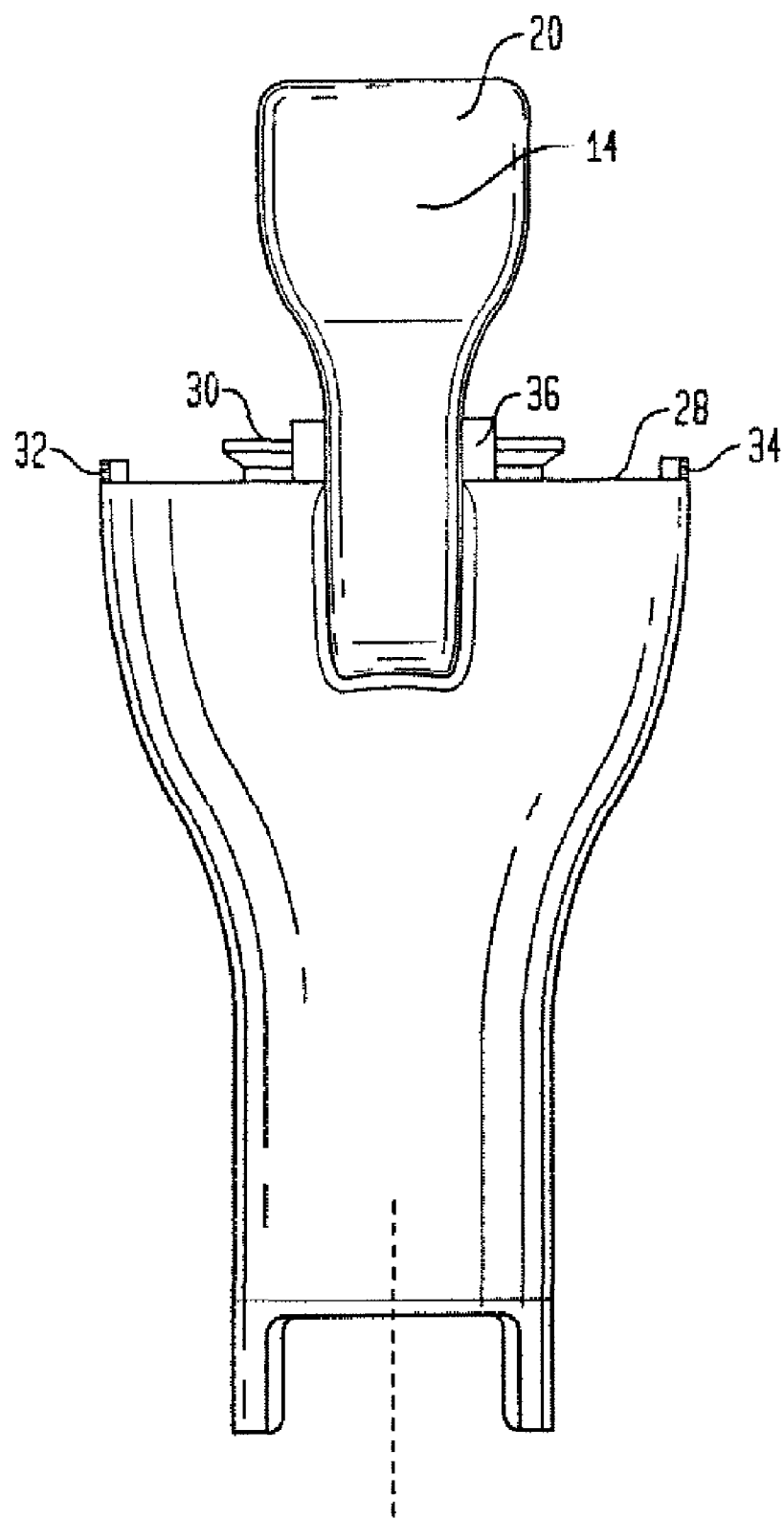
FIG. 1c is an anterior view of the prosthetic tibia shown in FIGS. 1a and 1b.
Figure 1D:
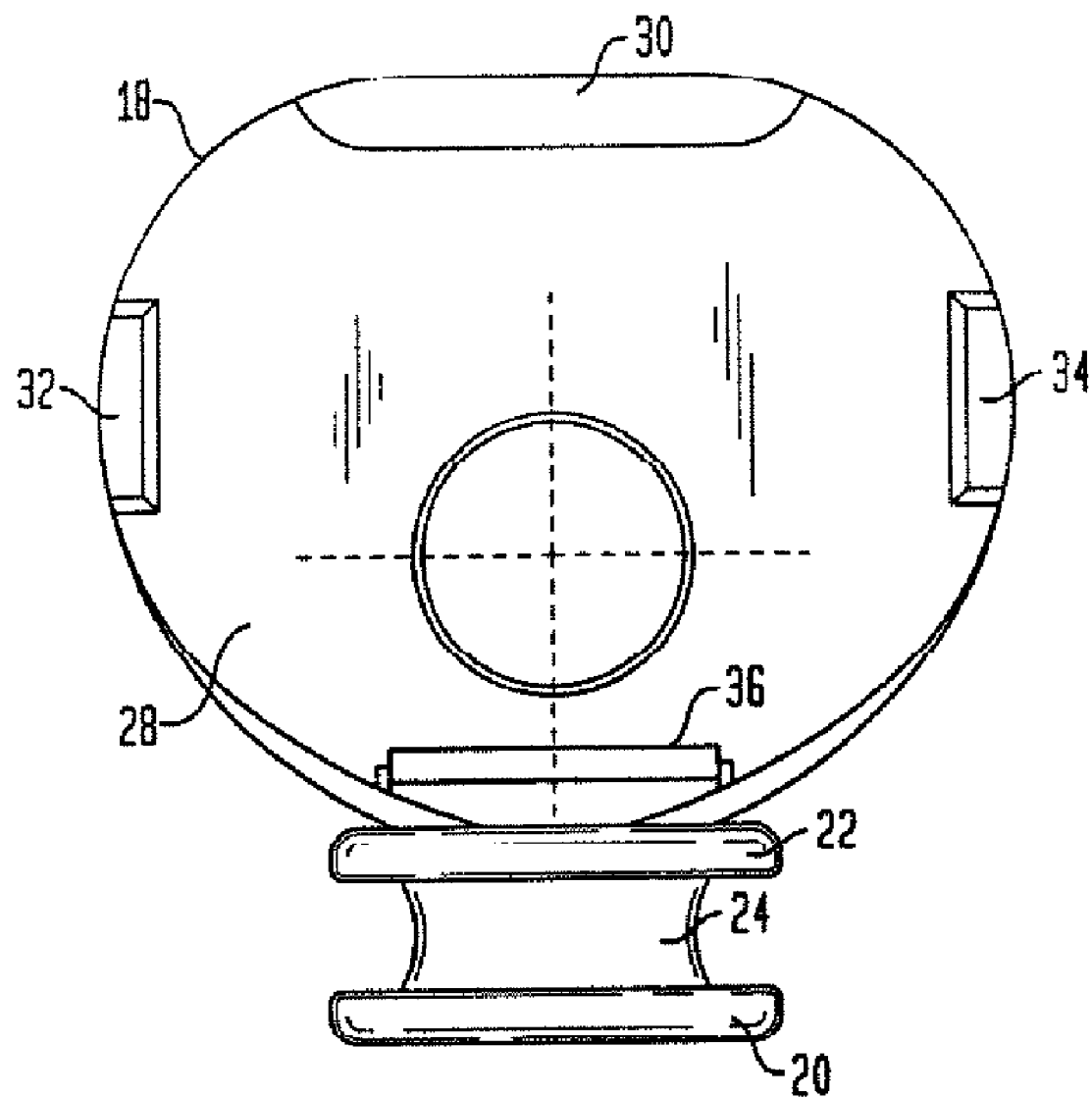
FIG. 1d is a top view of the prosthetic tibial components of FIGS. 1a through 1c showing the superior surfaces thereof.

In describing preferred embodiments of the medical device of the present technology, reference will be made to directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to the human body.

Referring to FIGS. 1a through 1d there is shown a preferred embodiment of a prosthetic tibial component generally denoted as 10, which may be part of modular oncology system such as disclosed in U.S. Pat. No. 4,578,081. In such a system large portions of diseased bones are removed and replaced by prosthetic implants such as the proximal tibia. The tibial prosthesis includes a proximal tibial portion 12 and a proximally extending soft tissue attachment device 14. In the preferred embodiment, soft tissue attachment device 14 includes a stem portion 16, which is coupled to the proximal end 18 of prosthetic tibia 12. The device 14 may be one-piece with the proximal tibia such as by being integrally cast therewith or welded thereon. Other techniques such as Selector Laser Melting (SLM) or compression molding may also be used.

Soft tissue attachment device 14 includes first and second arms 20 and 22, which form a generally U-shaped slot 24. Slot 24 is designed to receive a portion of the patellar tendon. Arms 20 and 22 merge at a junction 26 to form stem 16. In the preferred embodiment, the proximal superior facing surface of tibial prosthesis 12 is a planar surface 28. While a U-shaped slot is shown, other shape slots may also be used.

In the preferred embodiment, surface 28 includes four proximally extending flange portions 30, 32, 34, and 36. Flange portions 30, 32, 34, and 36 are designed to receive a prosthetic bearing surface which, in the preferred embodiment, is made of ultrahigh molecular weight polyethylene (UHMWPE). However, the bearing component may be made of other polymeric or metal materials suitable for prosthetic bearings. When a UHMWPE insert (not shown) is utilized, it may be snapped and locked in recessed grooves 38, 40, 42, and 44 formed in flanges 30, 32, 34, and 36, respectively.

Figure 2B:
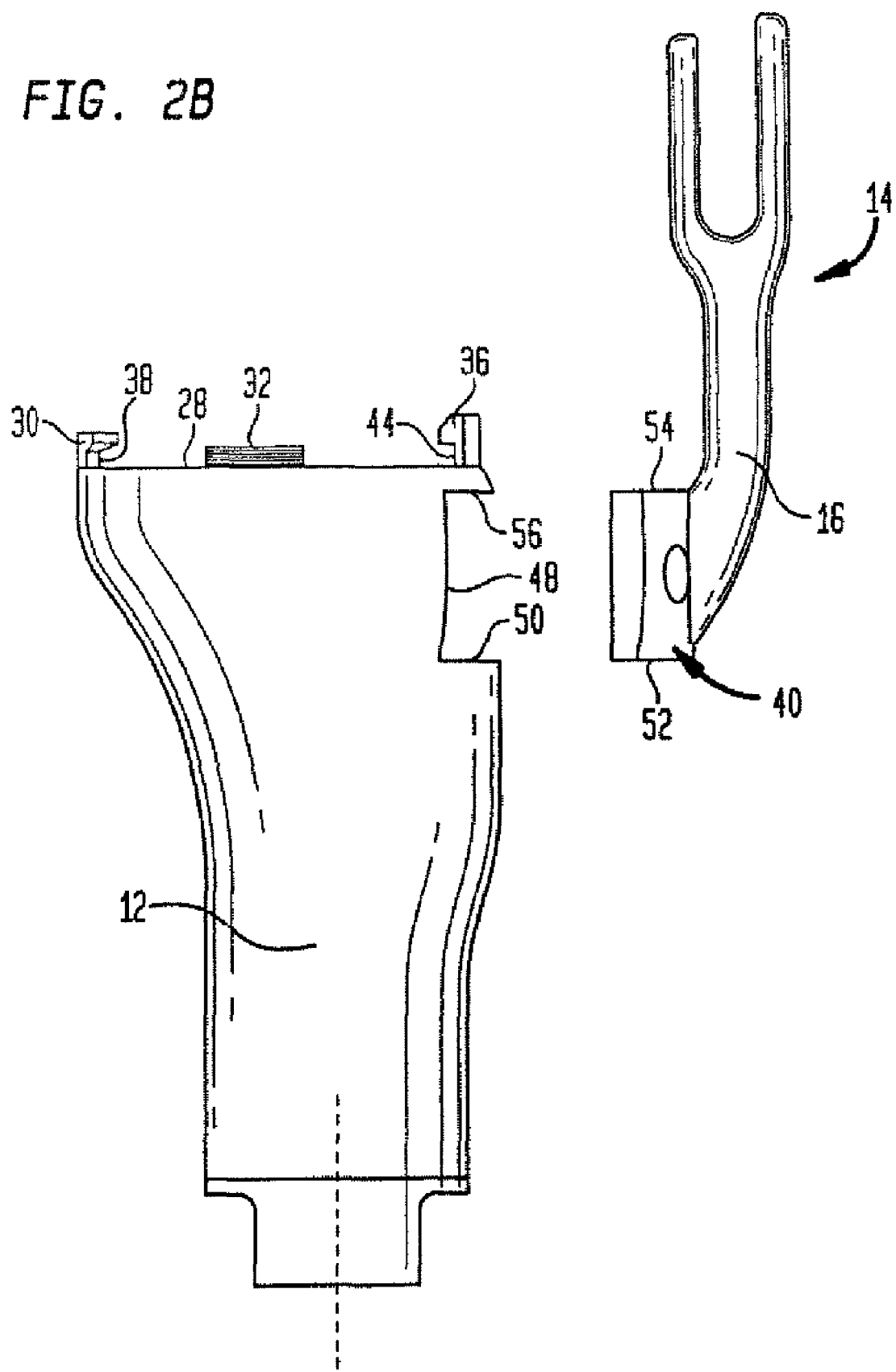
FIG. 2b is a lateral view of the tibia of FIG. 2a showing the soft tissue attachment device spaced anteriorly of the tibia.

Referring to FIGS. 2a and 2b, there is shown a modular connection between the proximally extending tendon attachment device 14 and the proximal portion 18 of tibia prosthesis 12. The modular attachment includes a flange or plate element 40 having a pair of through holes 42 for receiving screws (not shown), which engage with threaded bores 44 and 46 in tibial prosthesis 12. Threaded bores 44 and 46 are preferably formed in a recessed area 48 formed in the anterior facing surface of the proximal tibia portion 18. The recess preferably has a distal surface 50, which receives a bottom surface 52 of flange portion 40 of the proximally extending stem portion 16 tendon attachment device 14. Surface 50 provides support for distal surface 52. As discussed above, stem portion 16 is fixedly attached to or integral with flange portion 40. The stem portion 16 may be attached by welding so that the tendon attachment device 14 is made one piece with flange portion 40.

Referring to FIG. 2b, flange portion 40 includes a proximally facing surface 54, which engages a distally facing surface 56 on the recessed portion 48 of prosthetic tibial component 12. Thus flange portion 40, once assembled, is prevented from proximal-distal movement by surfaces 50 and 56 of recess 48.

Figure 3A:
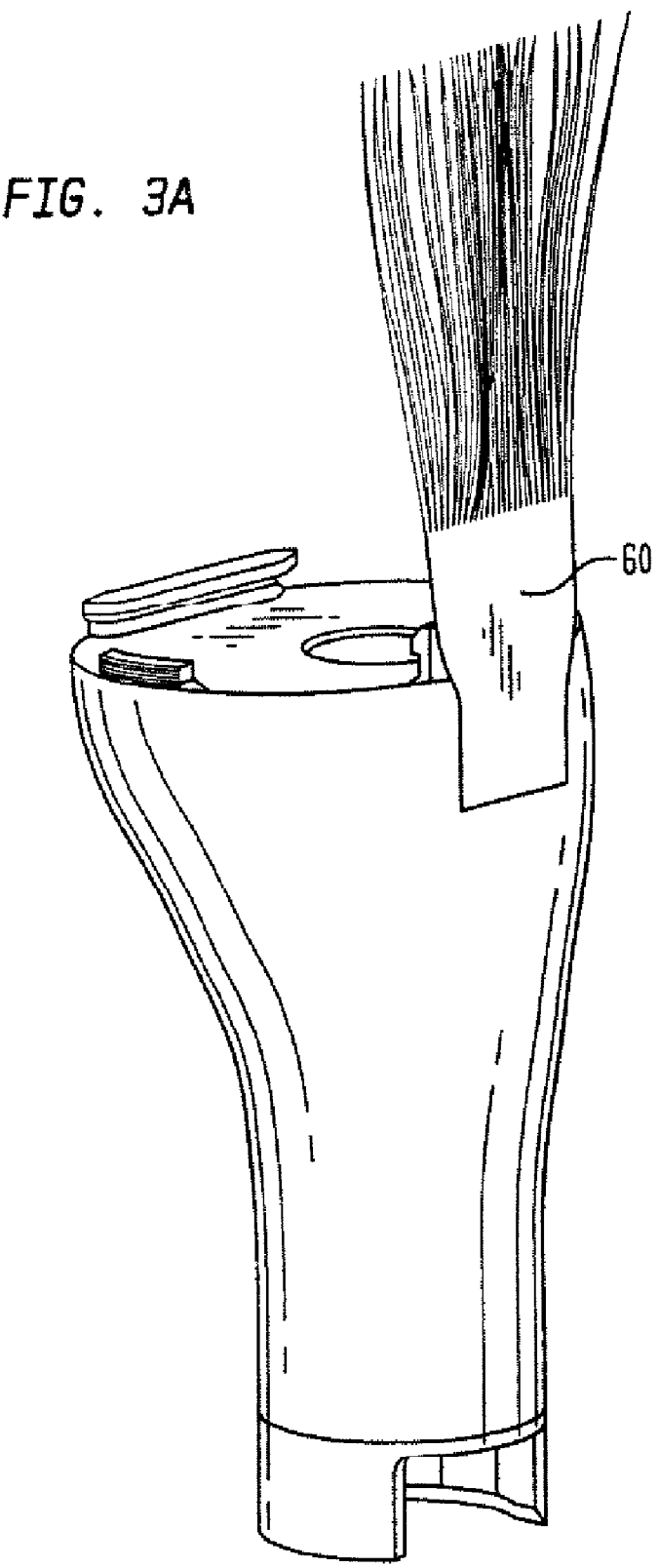
FIG. 3a is an alternate prosthetic component having a receptacle for receiving soft tissue as shown.
Figure 3B:
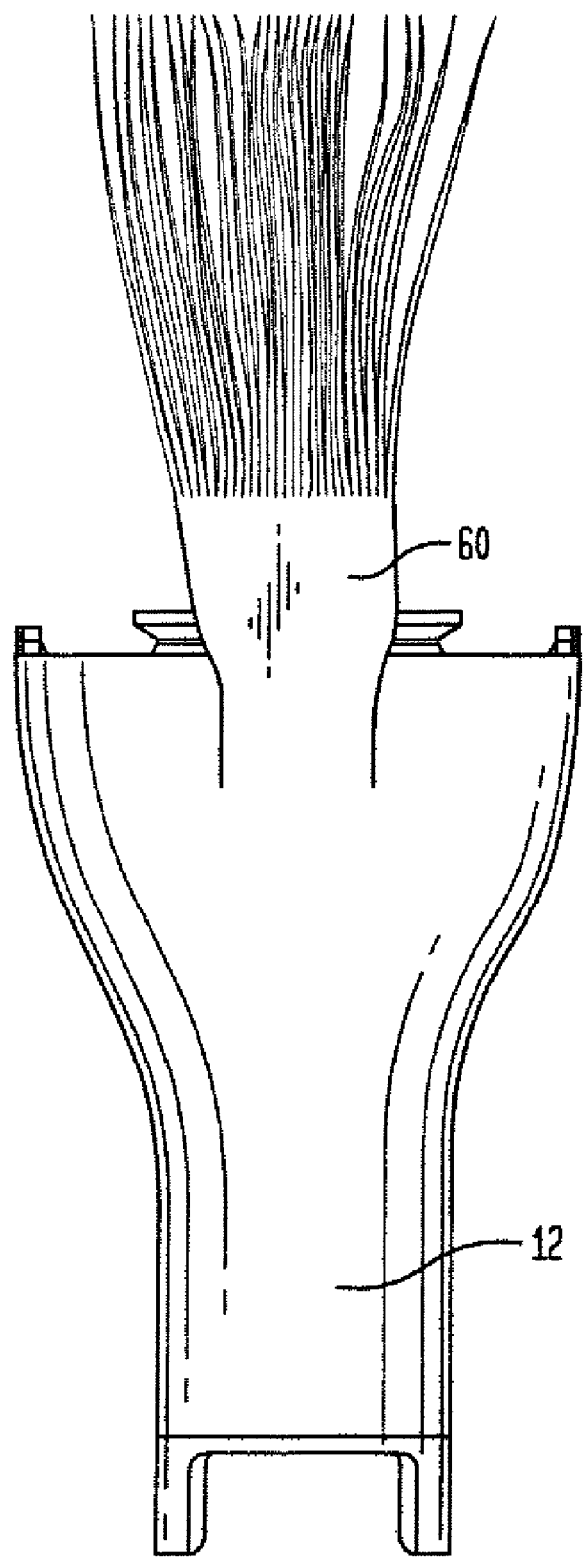
Figure 4B:
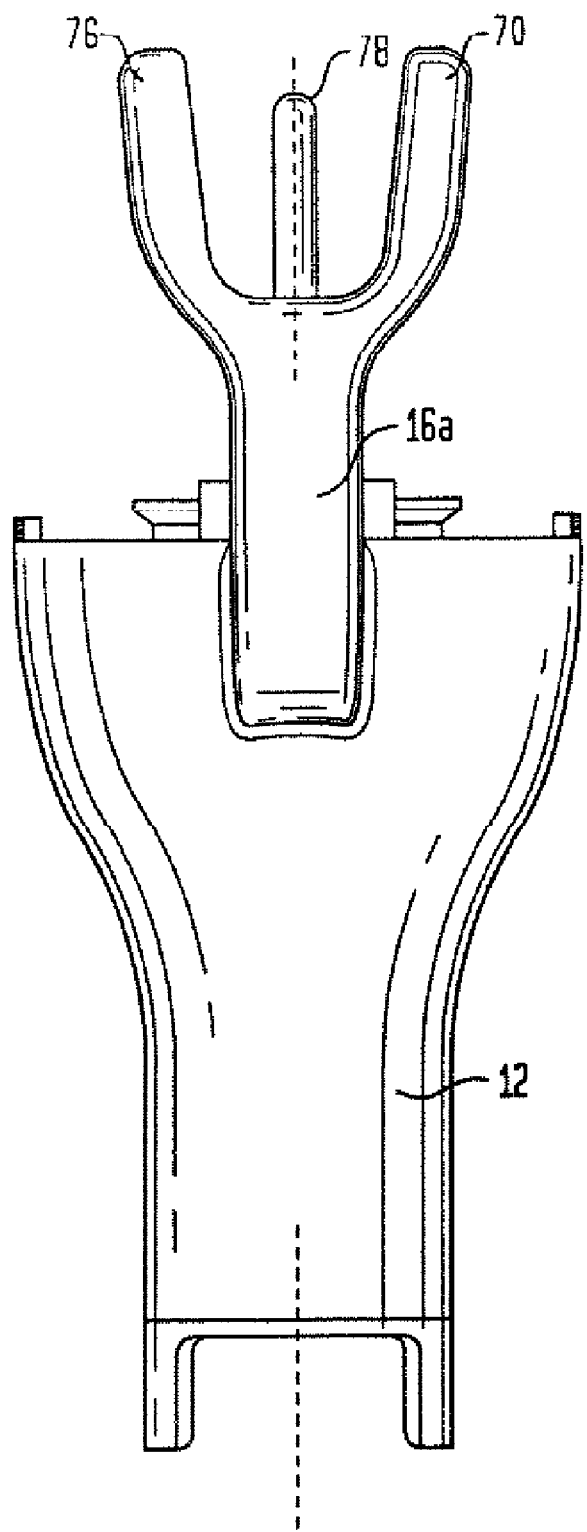
Figure 4C:
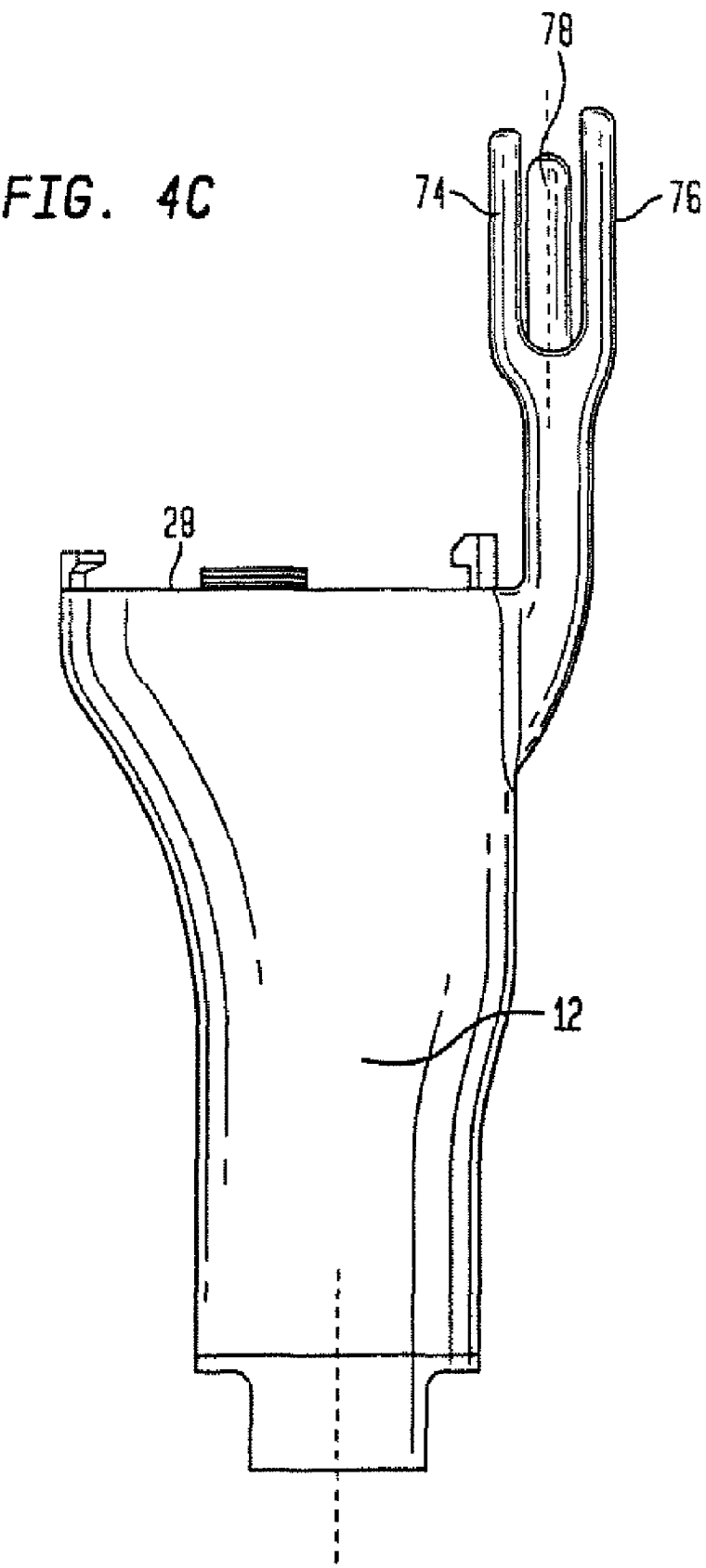
FIG. 4c is a lateral view of the prosthetic tibial components of FIGS. 4a and 4b.
Figure 4D:
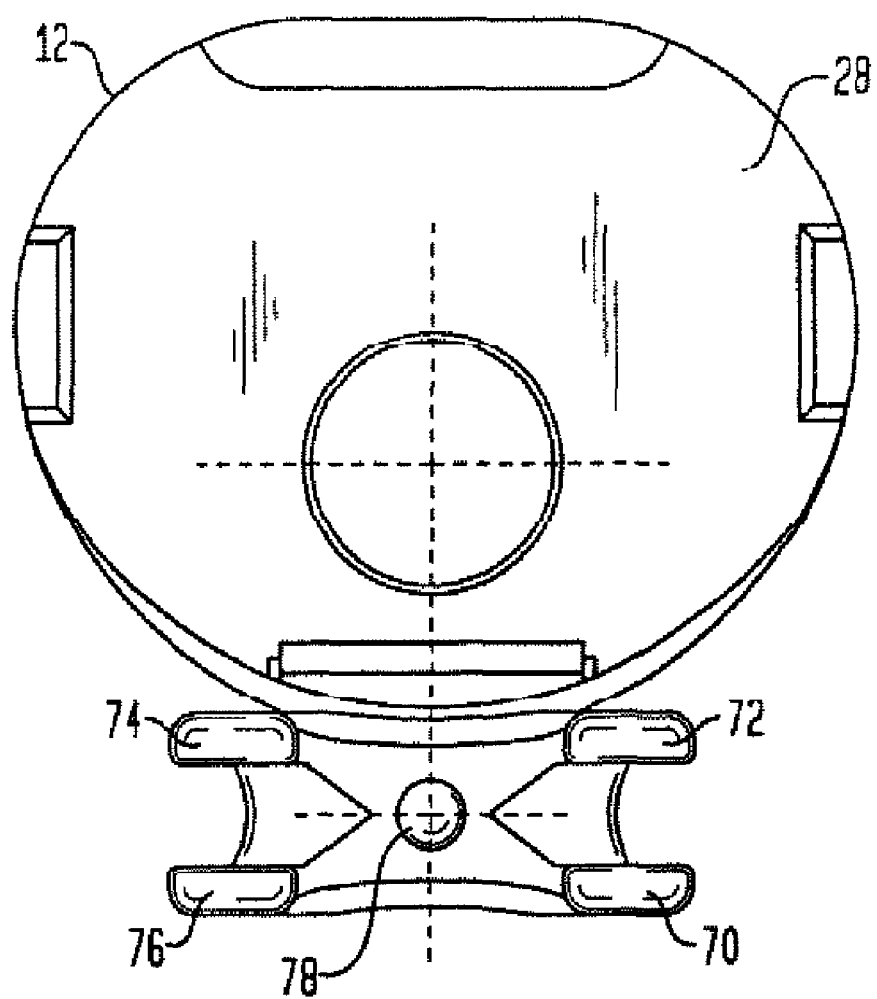
FIG. 4d is a top view of the prosthetic tibial component of FIGS. 4a through 4c joining the superior surface of the component.
Figure 5C:
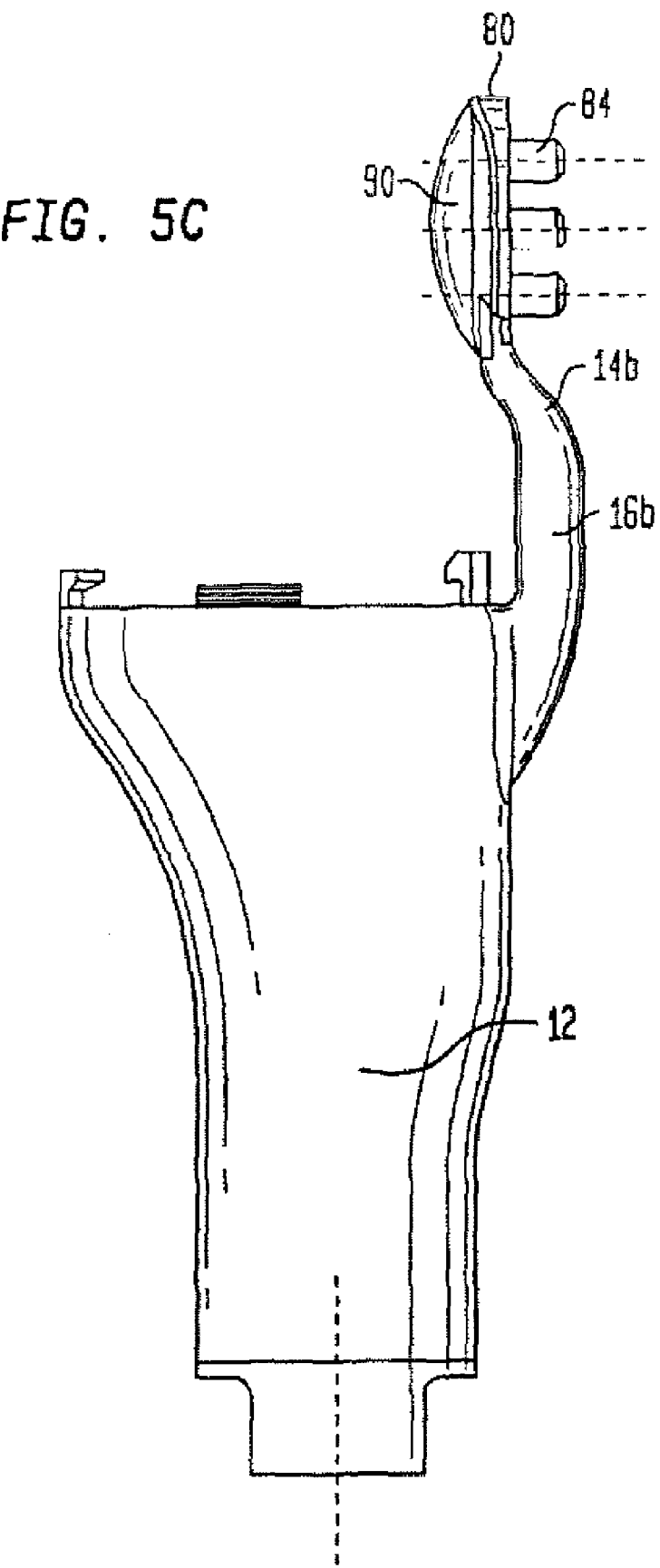
FIG. 5c is a lateral view of the prosthetic tibial component of FIGS. 5a and 5b.
Figure 5D:
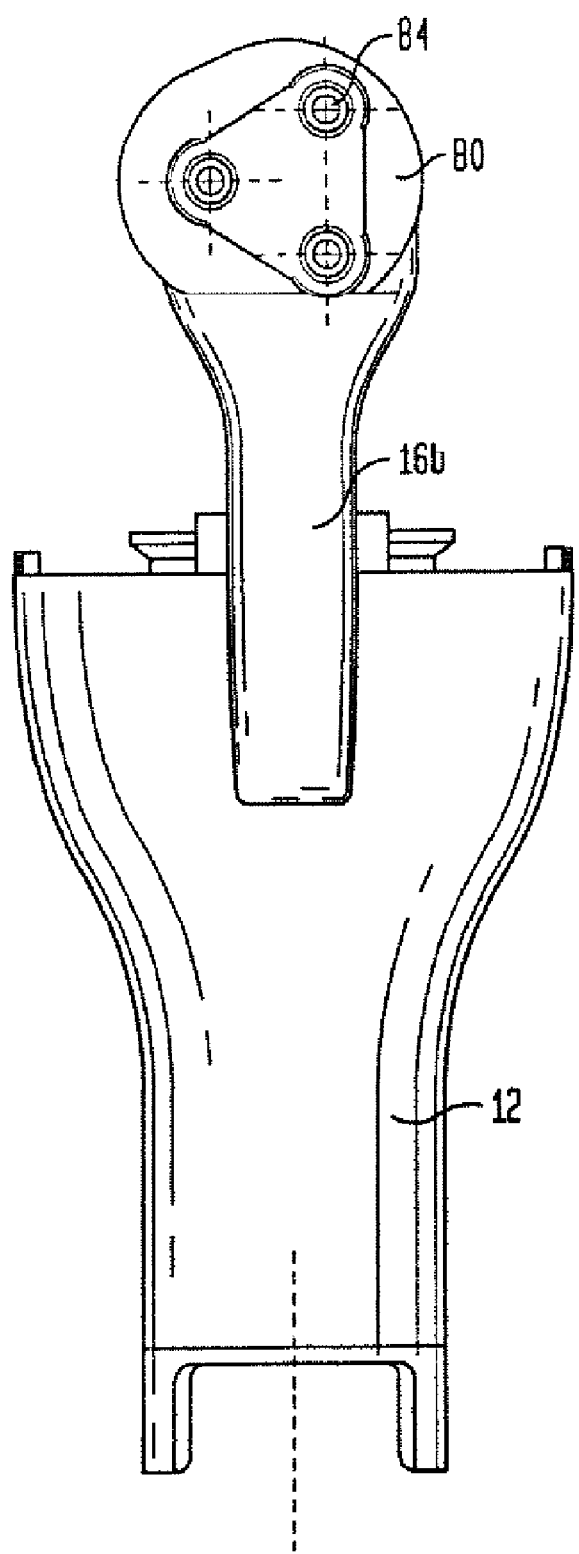
FIG. 5d is an anterior view of the soft tissue attachment device of FIGS. 5a-5c.
Figure 5E:
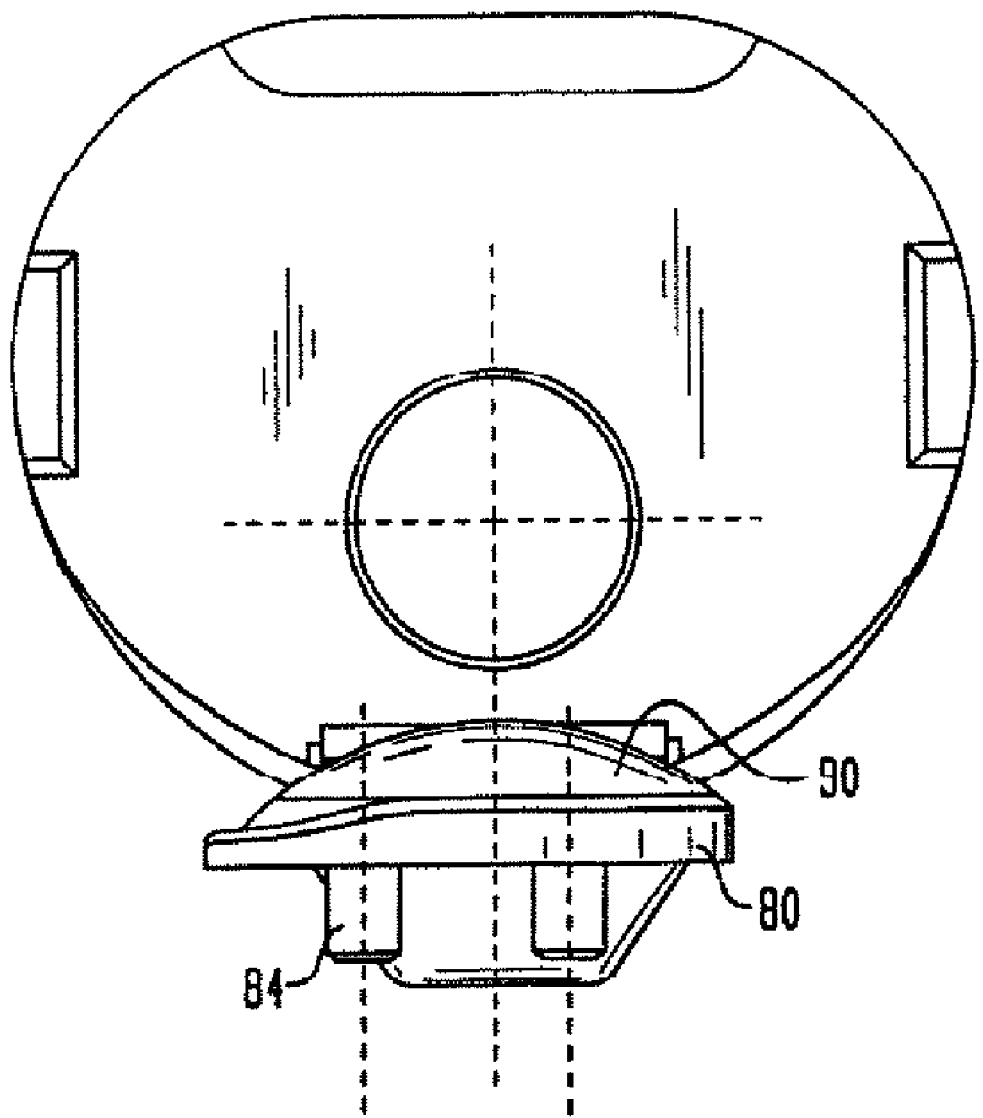
FIG. 5e is a top view of the prosthetic femoral components of FIGS. 5a-5d.

Referring to FIGS. 3a and 3b, there is shown an alternate method of attaching a tendon 60. In this embodiment the plurality of filaments are woven or stitched into soft tissue similar to suturing.

Referring to FIGS. 4a through 4d, there is shown yet an additional embodiment of the proximally extending tendon attachment device of the present invention. In this embodiment, prosthetic tibia 12 remains essentially unchanged with an alternate tendon attachment device 14a having a stem 16a attached to an anteriorly facing surface of proximal portion 18 of tibia prosthesis 12. The tendon attachment area includes four spaced arms 70, 72, 74, and 76, which form U-shaped open areas facing anteriorly and posteriorly as well as medially and laterally. A proximally facing elongate pin 78 is provided. The four spaced arms 70, 72, 74 and 76 are attached to the soft tissue in the same manner as described with respect to FIG. 1 after the plug is implanted into the patella for load sharing. Pin 78 can be cylindrical or can have other shapes.

Referring to FIGS. 5a through 5e, there is shown yet an additional design for the proximally extending tendon attachment device wherein, again the tibial prosthetic portion 12 remains the same. However, in this embodiment, a proximally extending tendon attachment device 14b includes a stem portion 16b attached to the anteriorly facing surface of the tibial prosthesis 12. A resurfacing portion 80 is provided at the proximal end of the stem 16b, which the resurfacing portion includes three pointed pins 82, 84, and 86. Pins 82, 84, and 86 extend anteriorly from an anterior surface 88 of resurfacing portion 80. The posterior surface of resurfacing element 80 includes a smooth portion 90, which may be part spherical in shape. Part spherical surface 90 may act as a prosthetic patellar surface once the patella is attached to pins 82, 84, and 86. In this embodiment, the stem 16b and attachment device 14b may extend anteriorly and proximally to locate surface 90 of resurfacing portion 80 at the proper location for engaging a trochlear groove of a prosthetic femoral component (not shown).

Figure 6A:
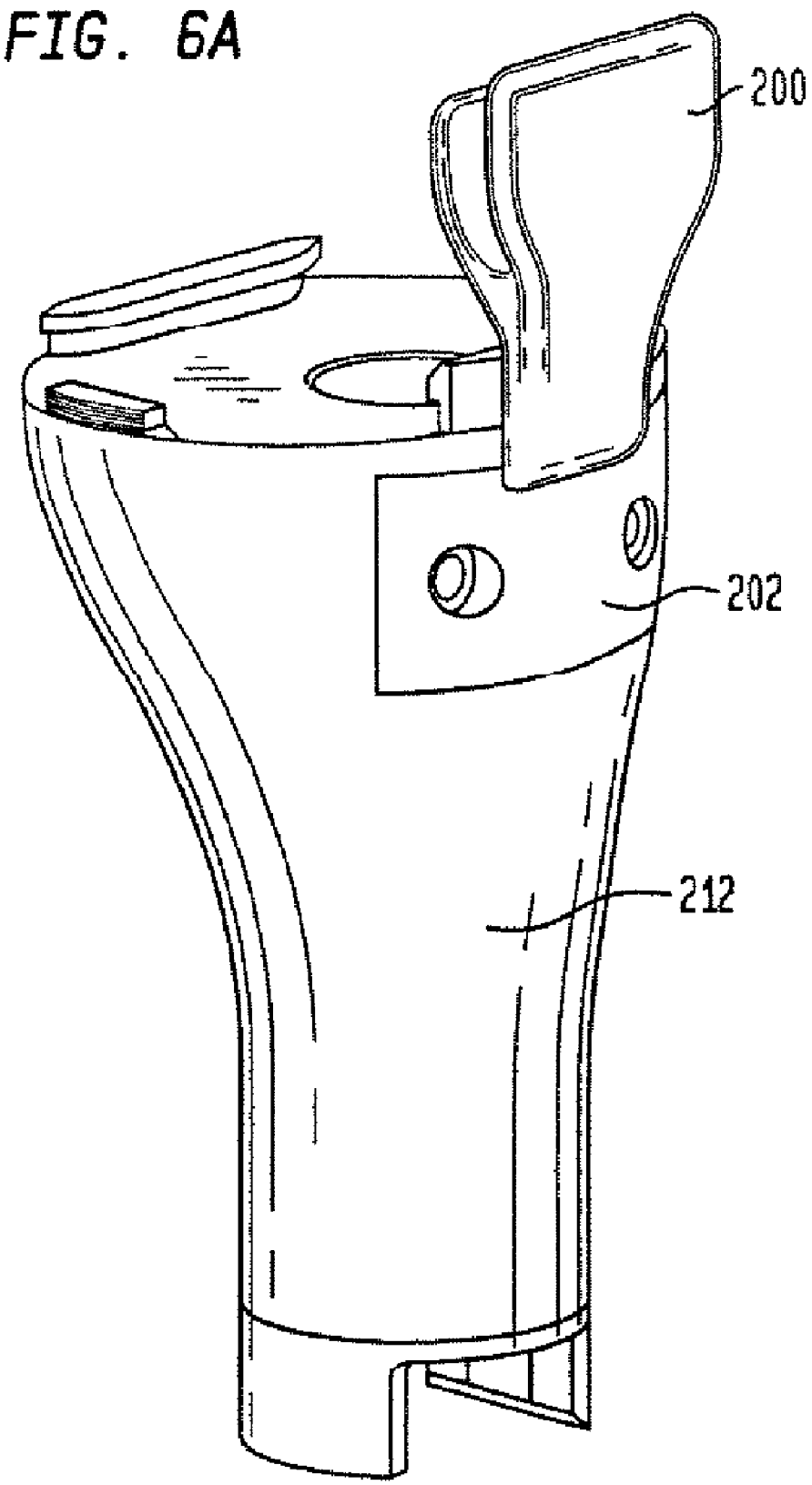
FIG. 6a is an isometric view of yet another embodiment of the soft tissue attachment device of the present invention.

Referring to FIGS. 6a and 6b there is shown an alternate embodiment in which a soft tissue attachment element such as a patellar tendon attachment element 200 is coupled to a prosthetic tibial component 212 by clamping element 202. Attachment element 200 has a curved distal portion 204 which sits in a groove 206 formed in a recess 208 in the anterior portion of component 212. Portion 204 is clamped within recess 206 by clamp 202. Clamp 202 includes a pair of apertures 210 for receiving screws (not shown) which thread into threaded bores 214 formed in the anterior surface of component 212 in the area of recess 208. Soft tissue attachment element 200 includes an anteriorly extending portion 216 which forms a proximal part of curved distal end portion 204. Portion 216 fits within cut-out 218 of clamp 202 when the soft tissue attachment element 200 is assembled as shown in FIG. 6A.

Figure 7A:
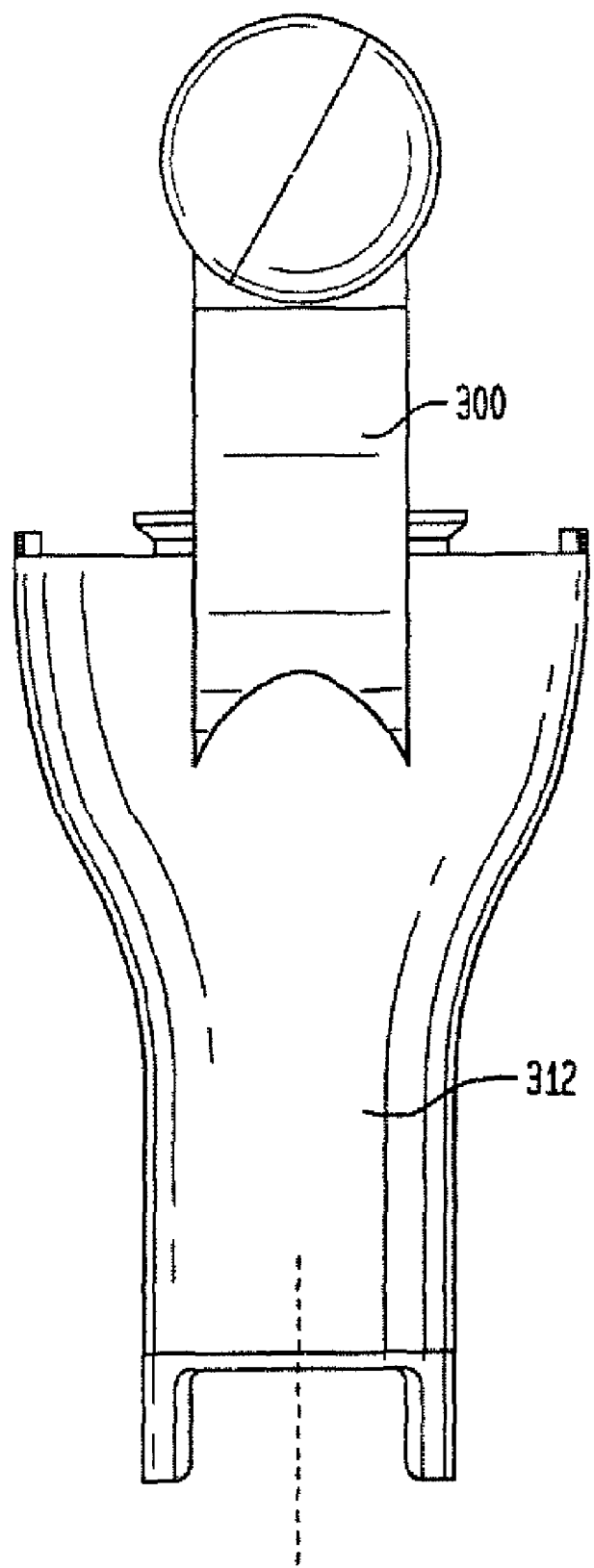
FIG. 7a is a front view of an additional embodiment of the present invention.
Figure 7B:
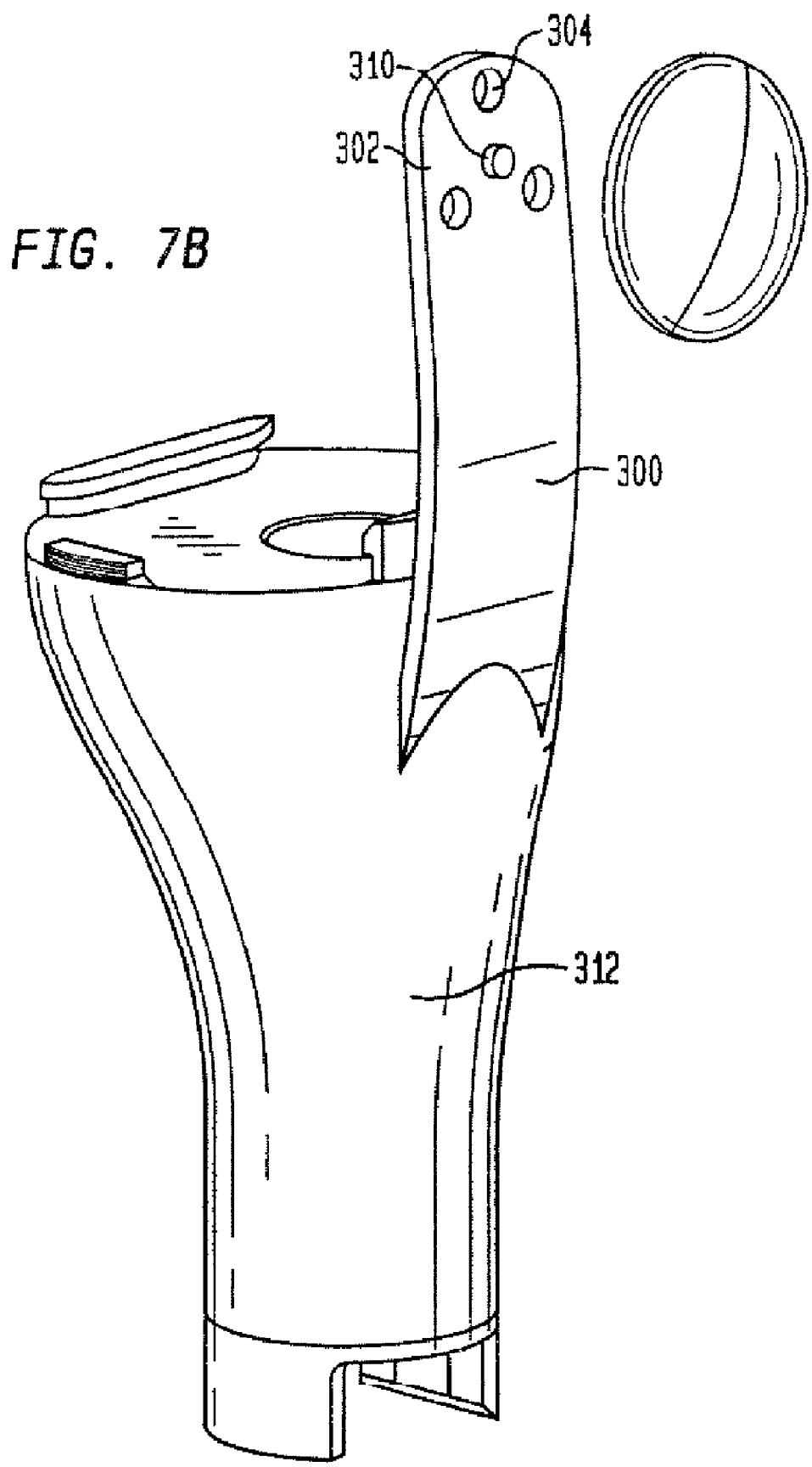
FIG. 7b is an isometric view of the ultimate embodiment of FIG. 7A with the prosthetic patellar element removed.

Referring to FIGS. 7a-7c, a proximal tibial component 312 with an integral soft tissue attachment element 300 integrally formed therewith such as by welding or casting. Soft tissue attachment element 300 includes a proximal end 302 having a plurality of through holes 304 for receiving the pegged posterior receiving peg elements 306 of a prosthetic patellar component 308. A small protrusion 310 is formed on the anterior face of proximal end 302 of soft tissue attachment element 300. Protrusion 310 extends into a recessed bore 312 formed on the posterior face of prosthetic patella 308. As in all of the other embodiments the proximal surface 328 includes locking elements 314 for fixing a ultra high molecular weight polyethylene bearing surface to the proximal tibia. Such structures are well known in the art.

While the soft tissue attachment element is described herein in relation to a tibia similar elements may be used with a femoral knee joint prosthesis component, an elbow prosthesis component or a humeral prosthetic component or any other suitable locations where soft tissue is attached to bone.

Although the technology herein has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology as defined by the appended claims.

The invention claimed is:

1. A prosthetic bone implant, the bone implant forming one side of a joint, comprising:
   a prosthesis for replacing one side of a joint, the prosthesis having a bearing surface located on one side of a joint line; and
   a soft tissue attachment component having a flange portion fixedly connected to the prosthesis adjacent at a first end and extending outwardly therefrom beyond the joint line at a second end, the soft tissue attachment component further comprises a stem portion formed as a one-piece construct with the flange portion, the stem portion having a free end with first and second arms forming a U-shaped slot, the U-shaped slot being open proximally at a free end thereof and having two medial and lateral side openings extending from the open free end of the slot distally towards the stem portion;
   wherein the soft tissue attachment component is moveable with respect to the prosthesis while connected thereto.

2. The prosthetic bone implant of claim 1, further comprising a plurality of filaments attached to the soft tissue attachment component, wherein the filaments are configured to connect the soft tissue attachment component to soft tissue.

3. The prosthetic bone implant of claim 1, wherein the soft tissue attachment component has a first end and a second end, the first end configured to attach to the prosthesis and the second end including a plug configured for attachment to bone.

4. The prosthetic bone implant of claim 1, wherein the soft tissue attachment component has a first end and a second end, the first end configured to attach to the prosthesis and the second end attached to a replacement or resurfacing element for a bony structure.

5. The prosthetic bone implant of claim 4, wherein the soft tissue attachment component is formed integrally with the replacement or resurfacing element.

6. The prosthetic bone implant of claim 1, wherein the soft tissue attachment component has a sufficient length to provide attachment to a piece of soft tissue that has been at least partially resected.

7. The prosthetic bone implant of claim 1, wherein the prosthesis and the soft tissue attachment mechanism are configured to be connected at the time of surgery.

8. The prosthetic bone implant of claim 1, wherein the soft tissue attachment component is configured to be modified by a surgeon according to the size and tension needs of a particular procedure.

9. The prosthetic bone implant of claim 1, wherein the soft tissue attachment component is composed of a material that is either synthetic or biologic, or a composite of synthetic and biologic materials.

10. The prosthetic bone implant of claim 1, wherein the soft tissue attachment component is composed of a material that is biodegradable or bioresorbable such that over time it is replaced by natural tissue.

11. The prosthetic bone implant of claim 1, wherein the soft tissue attachment component is at least partially porous.

12. The prosthetic bone implant of claim 1, wherein the soft tissue attachment component has a variable porosity throughout its length or throughout its cross section, or throughout both its length and its cross section.

13. The prosthetic bone implant of claim 9, wherein the soft tissue attachment component is composed at least in part of a material selected from the group consisting of Dacron, polytetra fluoroethylene, Texturized or Open-weave poly(ethylene terephthalate), waterswolen poly(2-hydroxyethyl methacrylate), polydioxanone, PDO/Elastin Weave, polyurethane, aromatic porous polyurethane, poly-(L-lactic acid), Polyetheretherketone, allograft or xenograft tendon or ligament, small-intestinal submucos, collagen, cell seeded collagen matrices, hydrogels, Chitosan, or other known cell scaffold materials.

* * * * *

UNITED STATES PATENT AND TRADEMARK OFFICE
Certificate

Patent No. 8,226,725 B2                                      Patented: July 24, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Ferko, Warwick, NY (US); and Mohamed Soliman, Piscataway, NJ (US).

Signed and Sealed this Twenty-ninth Day of July 2014.

THOMAS J. SWEET
*Supervisory Patent Examiner*
Art Unit 3738
Technology Center 3700

UNITED STATES PATENT AND TRADEMARK OFFICE
CERTIFICATE OF CORRECTION

PATENT NO. : 8,226,725 B2  
APPLICATION NO. : 12/551692  
DATED : July 24, 2012  
INVENTOR(S) : Michael C. Ferko and Mohamed Soliman Page 1 of 1

It is certified that error appears in the above-identified patent and that said Letters Patent is hereby corrected as shown below:

In the Specification

Col. 1, Line 16, insert -- a -- before "prosthesis"

Col. 1, Line 58, "requires" should read -- require --

Col. 2, Line 29, "tissues" should read -- tissue's --

Col. 4, Line 35, insert -- a -- before "modular oncology"

Signed and Sealed this  
Sixteenth Day of September, 2014

Michelle K. Lee  
*Deputy Director of the United States Patent and Trademark Office*